(12) United States Patent
Lee et al.

(10) Patent No.: US 11,903,957 B2
(45) Date of Patent: Feb. 20, 2024

(54) COMPOSITION FOR PREVENTING, AMELIORATING, OR TREATING SLEEP DISTURBANCE COMPRISING FLAVONOID COMPOUND AS EFFECTIVE COMPONENT

(71) Applicant: KOREA INSTITUTE OF ORIENTAL MEDICINE, Daejeon (KR)

(72) Inventors: Mi Young Lee, Seoul (KR); Yu Ri Kim, Daejeon (KR); Young Hwa Kim, Gyeonggi-do (KR); Bo-Kyung Park, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 458 days.

(21) Appl. No.: 17/284,592

(22) PCT Filed: Sep. 26, 2019

(86) PCT No.: PCT/KR2019/012499
§ 371 (c)(1),
(2) Date: Apr. 12, 2021

(87) PCT Pub. No.: WO2020/080697
PCT Pub. Date: Apr. 23, 2020

(65) Prior Publication Data
US 2021/0346417 A1    Nov. 11, 2021

(30) Foreign Application Priority Data
Oct. 17, 2018   (KR) .................. 10-2018-0123842

(51) Int. Cl.
*A61K 31/7048*   (2006.01)
*A23L 33/105*   (2016.01)
*A23L 33/125*   (2016.01)

(52) U.S. Cl.
CPC ........ *A61K 31/7048* (2013.01); *A23L 33/105* (2016.08); *A23L 33/125* (2016.08)

(58) Field of Classification Search
CPC ... A61K 31/7048; A23L 33/125; A61P 25/00; A23V 2200/322
See application file for complete search history.

(56) References Cited

U.S. PATENT DOCUMENTS

| | | |
|---|---|---|
| 2004/0185014 A1 | 9/2004 | Zuckerman |
| 2006/0198872 A1 | 9/2006 | Ikonte et al. |
| 2007/0196348 A1 | 8/2007 | Gardiner et al. |
| 2011/0026871 A1 | 11/2011 | Hatipoglu et al. |
| 2011/0268717 A1 | 11/2011 | Hatipoglu et al. |

FOREIGN PATENT DOCUMENTS

| | | |
|---|---|---|
| KR | 10-1112677 B1 | 2/2012 |
| KR | 10-2015-0019505 A | 2/2015 |
| KR | 10-1548325 B1 | 8/2015 |
| WO | WO 2007/026185 A2 | 3/2007 |
| WO | WO 2014/097259 A1 | 6/2014 |

OTHER PUBLICATIONS

Grundmann et al., Planta Med., 2008, 74, p. 1769-1773. (Year: 2008).*
Courts et al., Critical Reviews in Food Science and Nutrition, 2015, 55(10), p. 1352-1367. (Year: 2015).*
International Search Report for PCT/KR2019/012499 dated Jan. 3, 2020.
Jong-Min Woo et al., "Productivity Time Lost by Sleep Disturbance among Workers in Korea", J Korean Neuropsychiatr Assoc, vol. 50, pp. 62-68, 2011 (English Abstract is included in the first page.).
European Search Report For EP19874343.7 dated Jul. 11, 2022 from European patent office in a counterpart European patent application.
Elsas S-M el al., "*Passiflora incarnata* L. (Passionflower) extracts elicit GABA currents in hippocampal neurons in vitro, and show anxiogenic and anticonvulsant effects in vivo, varying with extraction method", Phytomedicine 17, 2010, pp. 940-949, doi:10.1016/j.phymed.2010.03.002.
Liselotte Krenn, "Die Passionsblume (*Passiflora incarnata* L.)—ein bewährtes pflanzliches Sedativum", 2002, Wiener Medizinische Wochenschrift vol. 152, No. 15-16, pp. 404-406, DOI:10.1046/j.1563-258X.2002.02062.x (English translation of summary in the first page is submitted herewith.).
Yu Ri Kim et al., "Effect of Hibiscus syriacus Linnaeus extract and its active constituent, saponarin, in animal models of stress-induced sleep disturbances and pentobarbital-induced sleep", Biomedicine & Pharmacotherapy, vol. 146, 2021, DOI: 10.1016/j.biopha.2021.112301.

* cited by examiner

Primary Examiner — Jonathan S Lau
(74) Attorney, Agent, or Firm — The PL Law Group, PLLC

(57) ABSTRACT

A method for treating sleep disturbance according to an embodiment of the present disclosure includes administering to a subject in need thereof a composition including saponarin of Chemical Formula 1, a salt thereof acceptable for use in food, or a hydrate thereof as an effective component: In an animal model with lack of sleep caused by caffeine, saponarin of the present invention restores the travel distance, mobility time, mobility frequency, and immobility time to normal as well as increases the mRNA expression of neuropeptide Y, cholecystokinin, and GABA A α1 receptor, thereby alleviating sleep disturbance. Therefore, the saponarin of the present invention can be advantageously used as a raw material for a functional health food or a pharmaceutical product for preventing, alleviating, or treating sleep disturbance.

6 Claims, 8 Drawing Sheets

Specification includes a Sequence Listing.

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Neuropeptide Y-F

<400> SEQUENCE: 1
aggcttgaag acccttccat                                           20

<210> SEQ ID NO 2
<211> LENGTH: 20
<212> TYPE: DNA
<213> ORGANISM: Artificial Sequence
<220> FEATURE:
<223> OTHER INFORMATION: Neuropeptide Y-R

<400> SEQUENCE: 2
acaggcagac tggtttcagg                                           20

<210> SEQ ID NO 3
<211> LENGTH: 20
<212> TYPE: DNA
<213> ORGANISM: Artificial Sequence
```

```
<220> FEATURE:
<223> OTHER INFORMATION: cholecystokinin-F

<400> SEQUENCE: 3
cgcgatacat ccagcaggtc                                               20

<210> SEQ ID NO 4
<211> LENGTH: 23
<212> TYPE: DNA
<213> ORGANISM: Artificial Sequence
<220> FEATURE:
<223> OTHER INFORMATION: cholecystokinin-R

<400> SEQUENCE: 4
aaatccatcc agcccatgta gtc                                           23

<210> SEQ ID NO 5
<211> LENGTH: 20
<212> TYPE: DNA
<213> ORGANISM: Artificial Sequence
<220> FEATURE:
<223> OTHER INFORMATION: GABA A alpha1 receptor-F

<400> SEQUENCE: 5
gccagaaatt ccctcccgaa                                               20

<210> SEQ ID NO 6
<211> LENGTH: 20
<212> TYPE: DNA
<213> ORGANISM: Artificial Sequence
<220> FEATURE:
<223> OTHER INFORMATION: GABA A alpha1 receptor-R

<400> SEQUENCE: 6
catcccacgc atacctctc                                                20

<210> SEQ ID NO 7
<211> LENGTH: 19
<212> TYPE: DNA
<213> ORGANISM: Artificial Sequence
<220> FEATURE:
<223> OTHER INFORMATION: GAPDH-F

<400> SEQUENCE: 7
aaggtggtga agcaggcat                                                19

<210> SEQ ID NO 8
<211> LENGTH: 21
<212> TYPE: DNA
<213> ORGANISM: Artificial Sequence
<220> FEATURE:
<223> OTHER INFORMATION: GAPDH-R

<400> SEQUENCE: 8
ggtccagggt ttcttactcc t                                             21
```

COMPOSITION FOR PREVENTING, AMELIORATING, OR TREATING SLEEP DISTURBANCE COMPRISING FLAVONOID COMPOUND AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/012499, filed Sep. 26, 2019, which claims priority to the benefit of Korean Patent Application No. 10-2018-0123842 filed in the Korean Intellectual Property Office on Oct. 17, 2018, the entire contents of which are incorporated herein by reference.

BACKGROUND

1. Technical Field

The present invention relates to a composition for preventing, ameliorating, or treating sleep disturbance comprising flavonoid compound as an effective component.

2. Background Art

Sleep is a state in which conscious activity is in rest with eyes closed, and it is an important process of restoring the energy consumed during daytime activity and recovering from the fatigue accumulated through physical activities. Sleep is not only a period during which energy restoration and fatigue recovery occur but also a period during which the growth hormone that is essentially required for human growth are secreted in the largest amount.

In human body, the brain governs all physiological functions for sustaining life and, for maintaining a suitably balanced activity, the brain needs a rest, which is mostly achieved during sleep. Due to the overwhelming and busy daily cycle of modern life, increased prevalence in obesity, population aging, and the like, the number of patients who are treated after diagnosis with sleep disturbance has increased in last several years. The number is expected to continue to rise in the coming years.

Among the various types of sleep disturbance, insomnia is one of the most common sleep disturbance and it is defined as a symptom of having difficulty with sleep like difficulty to fall asleep, difficulty to maintain sleep, shallow sleep, or poor sleep quality. Regardless of the stage of insomnia, it is reported that three in ten adults suffer from sleep disturbance and the ratio is even higher in women and seniors (J Korean Neuropsychiatr Assoc. 50: 62-8 (2011)).

The reason of having drastically reduced sleep duration by people in the modern world is based on various causes like an increase in mental disorders that are based on psychological reasons such as anxiety about future, depression, anxiety disorder, or stress, alternating day and night shifts resulting from diversity in jobs and society, unhealthy lifestyles, and the like. Namely, the more complex society becomes, the more jobs to be done and the more stress to be dealt with, yielding chronic sleep deficiency. In addition, drinking excess amounts of caffeinated beverages like coffee is also considered to be one reason of having sleep deficiency. Temporary acute insomnia easily occurs due to the irregular sleeping habit caused by temporary stress, change in sleeping habit, or the like. Temporary acute insomnia can be overcome when regular sleeping habit is practiced and underlying issues or stress for causing insomnia are removed so that normal sleeping habit can be restored. However, if a person continues to have a bad sleeping habit or deals with the insomnia in wrongful way, chronic insomnia in which he or she has trouble falling and/or staying asleep every night is caused. Symptoms of chronic insomnia impair the quality of life and increase a risk for depression by 10 times of more. In addition, sleep disturbance caused by insomnia increases the prevalence of various diseases by causing problems in controlling high blood pressure, blood sugar level, obesity or the like, and they also exhibit an influence on social aspect of a patient including higher medical cost, increased risk of having accidents during daytime, poor performance at work, or the like.

Meanwhile, it is known that saponarin ((1S)-1,5-anhydro-1-[7-(beta-D-glucopyranosyloxy)-5-hydroxy-2-(4-hydroxyphenyl)-4-oxo-4H-chromen-6-yl]-D-glucitol) is contained in extract of *Hibiscus syriacus*, barley sprouts, or the like. As a technique relating to saponarin, a composition for treating and preventing inflammatory disorder, immune disorder, or cancer comprising saponarin as an effective component is described in Korean Patent Registration No. 1112677. In Korean Patent Registration No. 1548325, a method of producing barley sprout with increased saponarin content by using irradiation of LED with blue light wavelength is described. However, so far there is no disclosure of a composition for preventing, ameliorating, or treating sleep disturbance comprising flavonoid compound as an effective component as it is described in the present invention.

SUMMARY

The present invention is devised under the circumstances that are described above. The present invention relates to a composition for preventing, ameliorating, or treating sleep disturbance comprising flavonoid compound as an effective component. Specifically, according to the finding that saponarin as the effective component of the present invention has an effect of not only restoring the travel distance, mobility time, mobility frequency, and immobility time to normal but also increasing the mRNA expression of neuropeptide Y, cholecystokinin, and GABA A α1 receptor in an animal model with lack of sleep caused by caffeine, the present invention is completed accordingly.

To achieve the purpose described above, the present invention provides a functional health food composition for preventing or ameliorating sleep disturbance comprising saponarin of the chemical formula 1, a salt thereof acceptable for use in food, or a hydrate thereof as an effective component.

The present invention further provides a pharmaceutical composition for preventing or treating sleep disturbance comprising saponarin of the chemical formula 1, a pharmaceutically acceptable salt thereof, or a hydrate thereof as an effective component.

The present invention relates to a composition for preventing, alleviating, or treating sleep disturbance comprising flavonoid compound as an effective component, and saponarin of the present invention has an effect of not only restoring the travel distance, mobility time, mobility frequency, and immobility time to normal but also increasing the mRNA expression of neuropeptide Y, cholecystokinin, and GABA A α1 receptor in an animal model with lack of sleep caused by caffeine.

DETAILED DESCRIPTION

Figure 1:
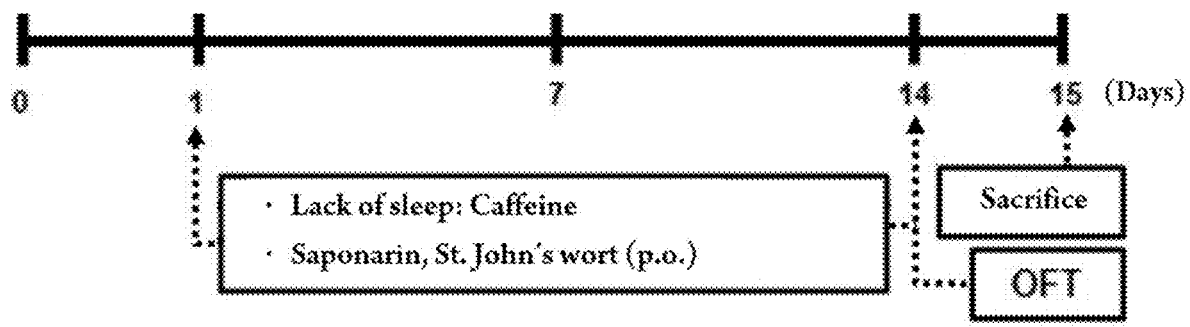
FIG. 1 is a diagram illustrating the process of carrying out a sleep disturbance test according to application of caffeine.

The present invention relates to a functional health food composition for preventing or ameliorating sleep disturbance comprising saponarin of the following chemical formula 1, a salt thereof acceptable for use in food, or a hydrate thereof as an effective component.

[Chemical formula 1]

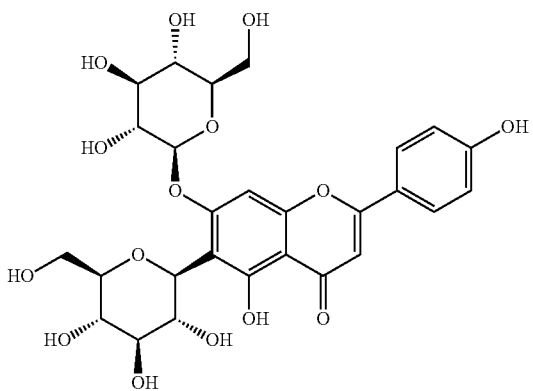

The sleep disturbance is characterized in that it is insomnia caused by stress or caffeine, but it is not limited thereto.

The functional health food composition of the present invention comprising saponarin of the chemical formula 1, a salt thereof acceptable for use in food, or a hydrate thereof as an effective component may be directly added to a food product or used with other food product or food ingredient, and it can be suitably used according to a common method. The mixing amount of the effective component can be suitably determined based on the purpose of use (i.e., prevention or amelioration). In general, the amount of the effective component to be comprised in the functional health food composition can be 0.1 to 90 parts by weight relative to the total weight of the functional health food composition. However, in case of long-term consumption under the purpose of maintaining good health and hygiene or managing health, it can be an amount below the aforementioned range, and, as there is no problem in terms of safety, the effective component may be also used in an amount above the aforementioned range.

The functional health food composition of the present invention is preferably produced in any one formulation selected from a powder, a granule, a pill, a tablet, a capsule, a candy, a syrup, and a drink, but it is not limited thereto.

When the functional health food composition of the present invention is consumed in the form of a beverage, other ingredients are not particularly limited except that, as an essential ingredient, the aforementioned effective component is comprised at indicated ratio, and, like common beverages, various flavors or natural carbohydrates can be comprised as an additional component. Examples of the natural carbohydrates include monosaccharides such as glucose or fructose, disaccharides such as maltose or sucrose, polysaccharides such as dextrin or cyclodextrin, and sugar alcohols such as xylitol, sorbitol, or erythritol. As a flavor other than those described above, natural flavor (thaumatin, *stevia* extract (e.g., rebaudioside A and glycyrrhizin)) and synthetic flavor (e.g., saccharine and aspartame) can be advantageously used.

The functional health food composition of the present invention may further comprise, in addition to the effective component, at least one selected from a nutritional supplement, a vitamin, an electrolyte, a flavor, a coloring agent, an enhancing agent, pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink. Other than those, fruit flesh for producing natural fruit juice or vegetable drink can be comprised in the functional health food composition of the present invention. The fruit flesh may be used either independently or in combination thereof. Ratio of the above various additives is not critical.

The present invention further relates to a pharmaceutical composition for preventing or treating sleep disturbance comprising saponarin of the following chemical formula 1, a pharmaceutically acceptable salt thereof, or a hydrate thereof as an effective component.

[Chemical formula 1]

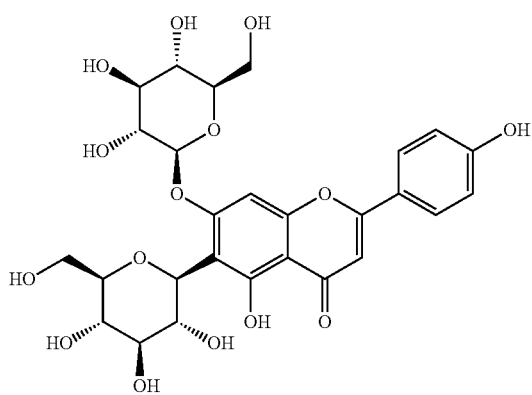

The pharmaceutical composition of the present invention can be prepared in various formulations including oral formulation and parenteral formulation. In case of preparing the composition in a formulation, the preparation can be made by using a carrier, a vehicle, or a diluent that are commonly used, but it is not limited thereto.

As for the solid preparation for oral administration, a tablet, a pill, a powder preparation, a granule, a capsule or the like are included, and such solid preparation is produced by mixing at least one compound with one or more vehicles such as starch, calcium carbonate, sucrose, lactose, or gelatin. Furthermore, other than simple vehicles, a lubricating agent such as magnesium stearate or talc is also used. For the liquid preparation for oral administration, a suspension, a solution preparation for internal use, an emulsion, a syrup preparation, or the like can be mentioned. Other than water or liquid paraffin as a commonly used simple diluent, various kinds of a vehicle such as moisturizing agent, sweetening agent, aromatic agent, or preservatives may be included.

Examples of a preparation for parenteral administration include a sterilized aqueous solution, a non-soluble agent, a suspension agent, an emulsion, a freeze-drying agent, and a suppository agent. As a water insoluble solvent or a suspending agent, propylene glycol, polyethylene glycol, or vegetable oil such as olive oil, and injectable ester such as ethylolate can be used. As a base for a suppository, witepsol, macrogol, tween 61, cacao fat, laurin fat, glycerol, gelatin, or the like can be used.

The pharmaceutical composition of the present invention can be administered either orally or parenterally. In case of parenteral administration, it is preferable to choose external application on skin, intraperitoneal, rectal, intravenous, muscular, subcutaneous, endometrium injection, or intracerebroventricular injection, but it is not limited thereto.

The pharmaceutical composition of the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder of a patient, activity of a pharmaceutical, sensitivity to a pharmaceutical, administration period, administration route, excretion ratio, time period for therapy, elements including a pharmaceutical used in combination, and other elements that are well known in the medical field. The composition of the present invention can be administered as a separate therapeutic agent, or it can be used in combination with other therapeutic agent. It can be administered in order or simultaneously with a conventional therapeutic agent. It can be also administered as single-dose or multi-dose. It is important to administer an amount which allows obtainment of the maximum effect with minimum dose while considering all of the aforementioned elements without having any side effect, and the dosage can be easily determined by a person skilled in the pertinent art.

The dosage of the composition of the present invention may vary depending on bodyweight, age, sex, health state, diet of a patient, administration period, administration method, excretion rate, and severeness of disorder. However, since the dosage may be increased or decreased depending on the administration route, severeness of obesity, sex, body weight, age or the like, the scope of the present invention is not limited by the aforementioned dosage in any sense.

Hereinbelow, the present invention is explained in greater detail in view of the Examples. However, the following Examples are given only for specific explanation of the present invention and it would be evident to a person who has common knowledge in the pertinent art that the scope of the present invention is not limited by them.

EXAMPLES

Production, Preparation, and Administration of Test Sample 30 mg/kg saponarin (Sigma-Aldrich, St. Louis, Mo., USA; dissolved in 0.5% CMC solution) and 200 mg/kg St. John's wort (dissolved in 0.5% CMC solution) were aliquoted to satisfy the administration amount and orally administered one hour before the caffeine administration. To the normal and stress control, 0.5% CMC solution was orally administered while 30 mg/kg saponarin was administered to the saponarin group and 200 mg/kg St. John's wort was administered to the positive control, in an amount of 0.1 ml for each.

Animal Model with Sleep Disturbance Induced by Caffeine

Nine-week old male C57BL/6 mouse with bodyweight of 20 to 22 g was obtained from DBL Co., Ltd. (Eumseong-Gun, Chungcheong-Bukdo, Korea). The animal was supplied with a sufficient amount of water and solid feed (not added with any antibiotics, Samyang Animal Feed Co.) till the test day, and it was used for the experiment after acclimation for 1 week under an environment with temperature of 22±2° C., humidity of 55±15%, and 12-hour light and dark cycle. The experiment was carried out as illustrated in FIG. 1. Chemicals were orally administered every day for 14 days in total, and, according to intraperitoneal administration of 10 mg/kg caffeine 1 hour thereafter, sleep disturbance was induced.

Open Field Test

Open field test is to determine sleep disturbance and amelioration level obtained by pharmaceutical in which the determination is made by measuring the voluntary movement of a mouse after entering an unfamiliar field for the first time. A mouse was placed at the center (30×30×30 cm) of a white box, which is made of white acryl, and then travel distance (total distance moved), mobility time, mobility frequency and immobility time for 1 hour were analyzed by using Video tracking software (Ethovision XT, Noldus, Nederland).

Measurement of mRNA Expression Level of Neuropeptide Y, Cholecystokinin, and GABA A α1 Receptor in Cerebral Cortex Expression pattern of the gene in cerebral cortex, which has been removed from each test animal upon the completion of the test, was determined by real-time PCR. The cerebral cortex tissues of a mouse were treated with RNAzolB (Tel-Test) to extract RNA, and then analyzed by cDNA and real-time PCR instrument using One-step SYBR Green PCR kit (AB science).

The cerebral cortex tissues were added with 500 μl of RNAzol(B), disrupted using a homogenizer, and then added with 50 μl of chloroform ($CHCl_3$) followed by mixing again for 15 seconds. The resultant was allowed to stand on ice for 15 minutes and centrifuged at 13,000 rpm. Accordingly, the supernatant in an amount of about 200 μl was obtained and admixed with 2-propanol (200 μl) followed by mild shaking. The mixture was allowed to stand on ice for 15 minutes. After centrifuge again at 13,000 rpm, the resultant was washed with 80% ethanol and dried for 3 minutes in vacuum pump to extract RNA. The extracted RNA was dissolved in 20 μl distilled water which has been treated with diethyl pyrocarbonate (DEPC), and, after the inactivation on a heating block at 75° C., used for the synthesis of first strand cDNA. For reverse transcription, the prepared total RNA (3 μg) was reacted with DNaseI (10 U/μl) 2U/tube for 30 minutes on a 37° C. heating block followed by denaturation for 10 minutes at 75° C. After adding 2.5 μl of 10 mM dNTPs mix, 1 μl of random sequence hexanucleotides (25 pmole/25 μl), and 1 μl of RNase inhibitor (20 U/μl) as an RNA inhibitor, 1 μl of 100 mM DTT, and 4.5 μl or 5×RT buffer (250 mM Tris-HCl, pH 8.3, 375 mM KCl, 15 mM $MgCl_2$), 1 μl of M-MLV RT (200 U/μl) was added again to the mixture, which was then adjusted to have final volume of 20 μl using DEPC-treated distilled water. The resulting reaction mixture (20 μl) was thoroughly mixed and then subjected to centrifugal precipitation at 2,000 rpm for 5 seconds. After the reaction for 45 minutes on 37° C. heating block, first-strand cDNA was synthesized, which was then allowed to stand at 95° C. for 5 minutes to inactivate M-MLV RT. Thus-obtained cDNA after complete synthesis was used for PCR (polymerase chain reaction). Real time quantitative PCR was carried out by using Applied Biosystems 7500 Real-Time PCR system (Applied Biosystems, USA).

TABLE 1

Primer sequences of neuropeptide Y, cholecystokinin, and GABA A α1 receptor

| Gene | | Primer sequence |
|---|---|---|
| Neuropeptide Y | forward (SEQ ID NO: 1) | 5'-AGGCTTGAAGACCCTTCCAT-3' |
| | reverse (SEQ ID NO: 2) | 5'-ACAGGCAGACTGGTTTCAGG-3' |
| Cholecystokinin | forward (SEQ ID NO: 3) | 5'-CGCGATACATCCAGCAGGTC-3' |
| | reverse (SEQ ID NO: 4) | 5'-AAATCCATCCAGCCCATGTAGTC-3' |
| GABA Aα1 receptor | forward (SEQ ID NO: 5) | 5'-GCCAGAAATTCCCTCCCGAA-3' |
| | reverse (SEQ ID NO: 6) | 5'-CATCCCACGCATACCCTCTC-3' |
| GAPDH | forward (SEQ ID NO: 7) | 5'-AAGGTGGTGAAGCAGGCAT-3' |
| | reverse (SEQ ID NO: 8) | 5'-GGTCCAGGGTTTCTTACTCCT-3' |

Stress-Caused Sleep Disturbance Test—Test Sample Administration and Classification of Test Group The saponarin administration group was administered orally with 0.1 ml of saponarin, 30 minutes before the stress application. The normal and stress control were administered orally with 0.1 ml of a solvent. Operation was carried out for four divided groups, i.e., normal, control, saponarin, and positive control (St. John's wort), and total 24 animals were used, i.e., 6 animals per group.

Operation for Electroencephalography (EEG)

A male rat (7 week old) was suitably fed with solid feed and water till the test day. After the acclimation for 1 week in an environment in which temperature of 23 to 25° C., humidity of 45 to 60%, and illuminance of 200 to 300 LUX, and 12 hour light and dark cycle are maintained, the animals were subjected to the test. For the operation, a 7-week old Sprague Dawley (SD) rat was anesthetized by intraperitoneal injection of 40 mg/kg pentobarbital, and then placed and fixed on a stereotaxic instrument (Stoelting CO, USA) such that the bregma and lambda are in horizontal alignment. After suppressing subgaleal bleeding, hairs were shaved and the skull was exposed by excising the scalp and removing the periosteum. Based on the anatomy drawing by Paxinos & Watson, a hole was created by using drill, an electrode was inserted to reach the dura mater, and an electrode composed of two silver wires was inserted to neck muscle to record an electromyogram. On top of the cranial bone of cerebellum, pins attached with an electrode for recording an electroencephalogram and an electrode for recording an electromyogram were placed and fixed on top of the cranial bone by applying dental cement. Rat after the operation was placed in a cage in a breeding room, one rat per cage, and then allowed to recover for one week.

Animal Model with Sleep Disturbance Induced by Stress

Figure 7:
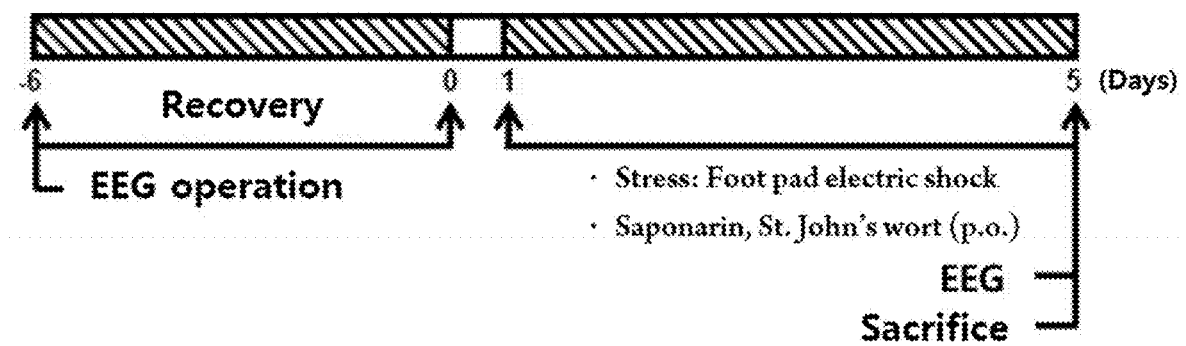
FIG. 7 is a diagram illustrating the process of carrying out a sleep disturbance test according to application of stress.

After the recovery from operation, the test was carried out as summarized in FIG. 7. A foot pad electric shock stress test was then performed every day for 5 days in total. To induce sleep disturbance, an electric shock at strength of 1 mA was randomly applied for 5 minutes (10 times per 3 seconds) to a foot pad of the rat.

Electroencephalography (EEG) Measurement

After the stress for 5 days, the rat was orally administered with each pharmaceutical, and, after 30 minutes, EEG recording was carried out in a light-blocking acrylic cylinder (PM 8:00 to AM 8:00). The wake time and sleep (REM and NonREM) time were recorded by using SleepSign Ver. 3 Software (Kissei Comtec, Nagano, Japan), which is a professional program for analyzing animal sleep.

Sleep Disturbance Test Using Caffeine—Production and Preparation of Test Sample 30 mg/kg saponarin (Sigma-Aldrich, St. Louis, Mo., USA; dissolved in 0.5% CMC solution) and 200 mg/kg St. John's wort (dissolved in 0.5% CMC solution) were aliquoted to satisfy the administration amount and orally administered one hour before the caffeine administration. To the normal and stress control, 0.5% CMC solution was orally administered while 30 mg/kg saponarin was administered to the saponarin group and 200 mg/kg St. John's wort was administered to the positive control.

<Statistical Treatment>

The results are given in mean±standard deviation, and the statistical comparison among test groups was achieved by carrying out one-way measures analysis of variance (ANONA) based on Tukey's Honest Significant Difference (HSD). $p < 0.05$ was taken to have statistical significance.

Example 1. Determination of Effect of Flavonoid Compound on Travel Distance of C57BL/6 Mouse with Induced Sleep Disturbance To determine the effect of saponarin exhibited on open-field travel distance of a C57BL/6 mouse with induced sleep disturbance, via oral administration according to the aforementioned experimental method, the normal and the control were administered orally with a solvent while the positive control was administered with 200 mg/kg St. John's wort. The saponarin administration group was orally administered with 30 mg/kg saponarin. After one hour, the animal was intraperitoneally administered with 10 mg/kg caffeine to induce sleep disturbance caused by caffeine for 14 days. Then, travel distance of the mouse was measured.

Figure 2:
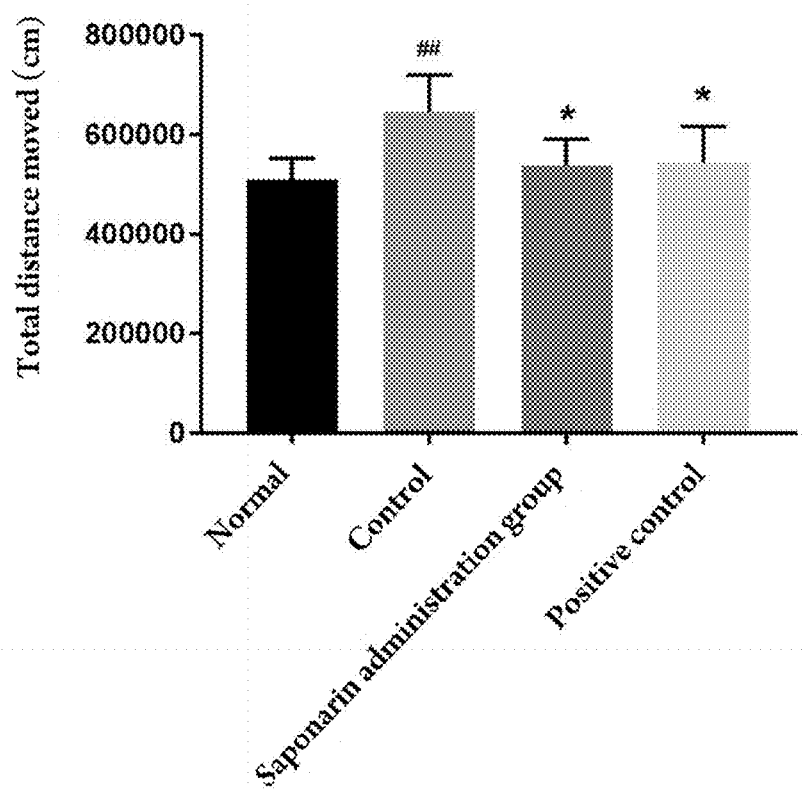
FIG. 2 shows the result of travel distance according to open field test which was measured, after administering for 14 days 30 mg/kg saponarin or 200 mg/kg St. John's wort (positive control) to a C57BL/6 mouse induced to have sleep disturbance by caffeine, on the last day of the administration. ## indicates that, compared to the normal, the control with induced sleep disturbance has increased travel distance in statistically significant sense, in which p<0.01. * indicates that, compared to the control, the saponarin administration group of the present invention and the positive control have decreased travel distance in statistically significant sense, in which p<0.05.

As the result is shown in FIG. 2, it was found that the travel distance has increased in significant sense in the control, while it has decreased in significant sense in the saponarin group and the group administered with positive control.

Example 2. Determination of Effect of Flavonoid Compound on Open-Field Mobility Time and Mobility Frequency of C57BL/6 Mouse with Induced Sleep Disturbance To determine the effect of saponarin exhibited on mobility time and mobility frequency of a C57BL/6 mouse with induced sleep disturbance, the animal was orally administered with a test sample and then intraperitoneally administered with caffeine for 14 days. Then, the mobility time and mobility frequency were measured.

Figure 3:
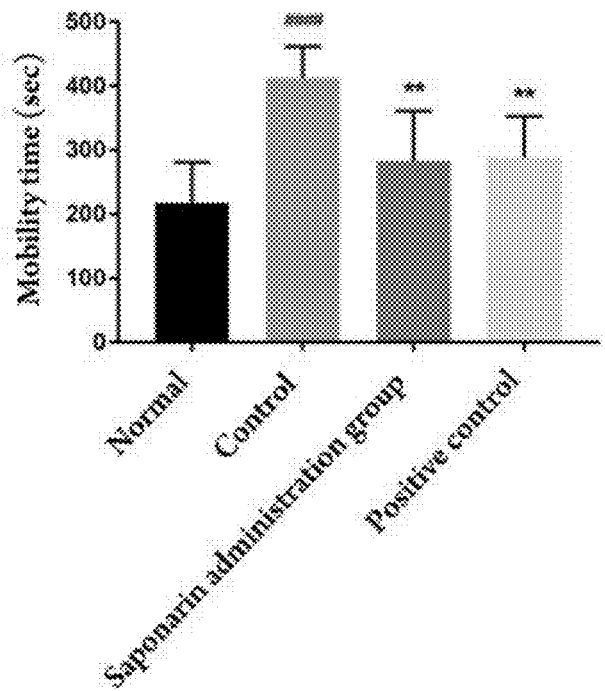
FIG. 3 shows the result of determining (A) mobility time and (B) mobility frequency according to open field test which was measured, after administering for 14 days 30 mg/kg saponarin or 200 mg/kg St. John's wort (positive control) to a C57BL/6 mouse induced to have sleep disturbance by caffeine, on the last day of the administration. #### indicates that, compared to the normal, the control with induced sleep disturbance has increased mobility time and increased mobility frequency in statistically significant sense, in which p<0.0001. ** indicates that, compared to the control, the saponarin administration group of the present invention and the positive control have decreased mobility time and decreased mobility frequency in statistically significant sense, in which p<0.01.
Figure 3:
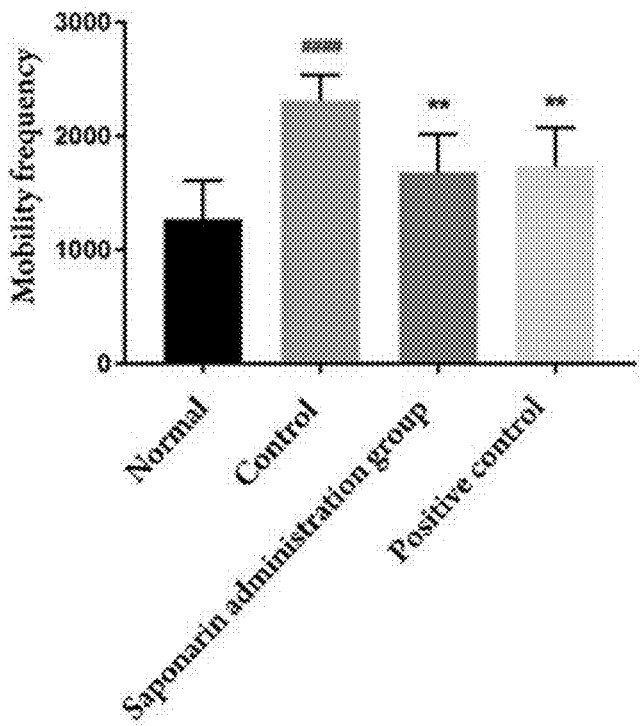

As the result is shown in FIG. 3, it was found that the mobility time and mobility frequency have increased in significant sense in the control, while they have decreased in significant sense in the saponarin group and the group administered with positive control.

Example 3. Determination of Effect of Flavonoid Compound on Open-Field Immobility Time of C57BL/6 Mouse with Induced Sleep Disturbance To determine the effect of saponarin exhibited on immobility time of a C57BL/6 mouse with induced sleep disturbance, the animal was orally administered, according to the aforementioned experimental method, with a test sample and then intraperitoneally administered with caffeine for 14 days. Thereafter, the immobility time of mouse was measured.

Figure 4:
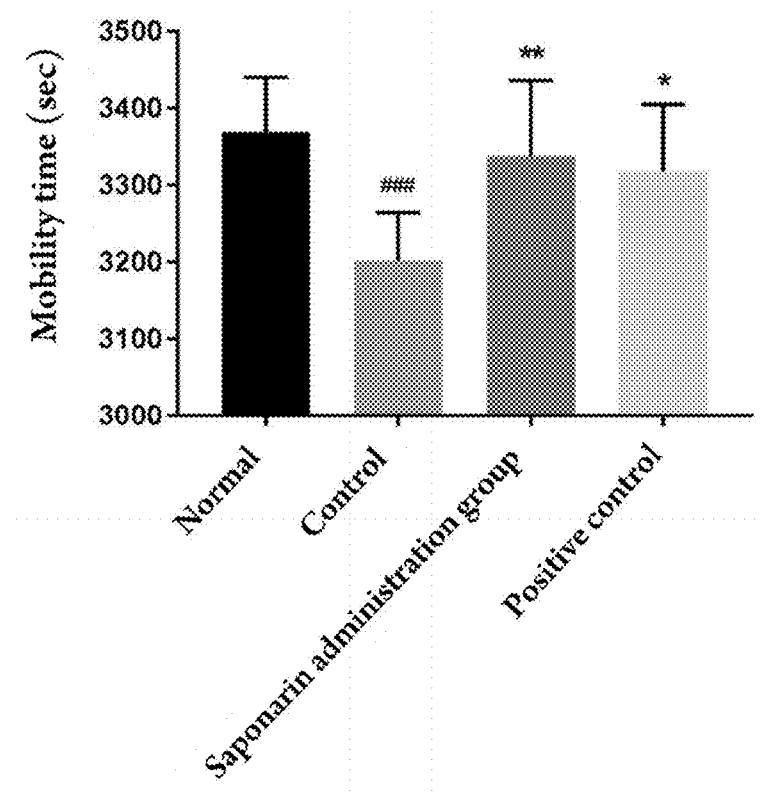
FIG. 4 shows the result of immobility time according to open field test which was measured, after administering for 14 days 30 mg/kg saponarin or 200 mg/kg St. John's wort (positive control) to a C57BL/6 mouse induced to have sleep disturbance by caffeine, on the last day of the administration. ### indicates that, compared to the normal, the control with induced sleep disturbance has decreased immobility time in statistically significant sense, in which p<0.001. *, ** indicate that, compared to the control, the saponarin administration group of the present invention and the positive control have increased immobility time in statistically significant sense, in which p<0.01.

As the result is shown in FIG. 4, it was found that the immobility time after sleep disturbance has decreased in significant sense in the control, while it has increased in the saponarin group and the group administered with positive control.

Example 4. Determination of Effect of Flavonoid Compound on mRNA Expression of Neuronal Protein, which is Expressed in GABAergic Neurons, in C57BL/6 Mouse with Induced Sleep Disturbance To examine any influence of saponarin exhibited on the mRNA expression of neuropeptide Y and cholecystokinin in cerebral cortex of C57BL/6 mouse which has been induced to have sleep disturbance, the animal was orally administered, according to the aforementioned experimental method, with a test sample and then intraperitoneally administered with caffeine for 14 days. Thereafter, cerebral cortex was collected by autopsy of the mouse to obtain RNA. cDNA was then prepared and mRNA expression of neuropeptide Y and cholecystokinin was analyzed by using real-time gene analyzer.

Figure 5:
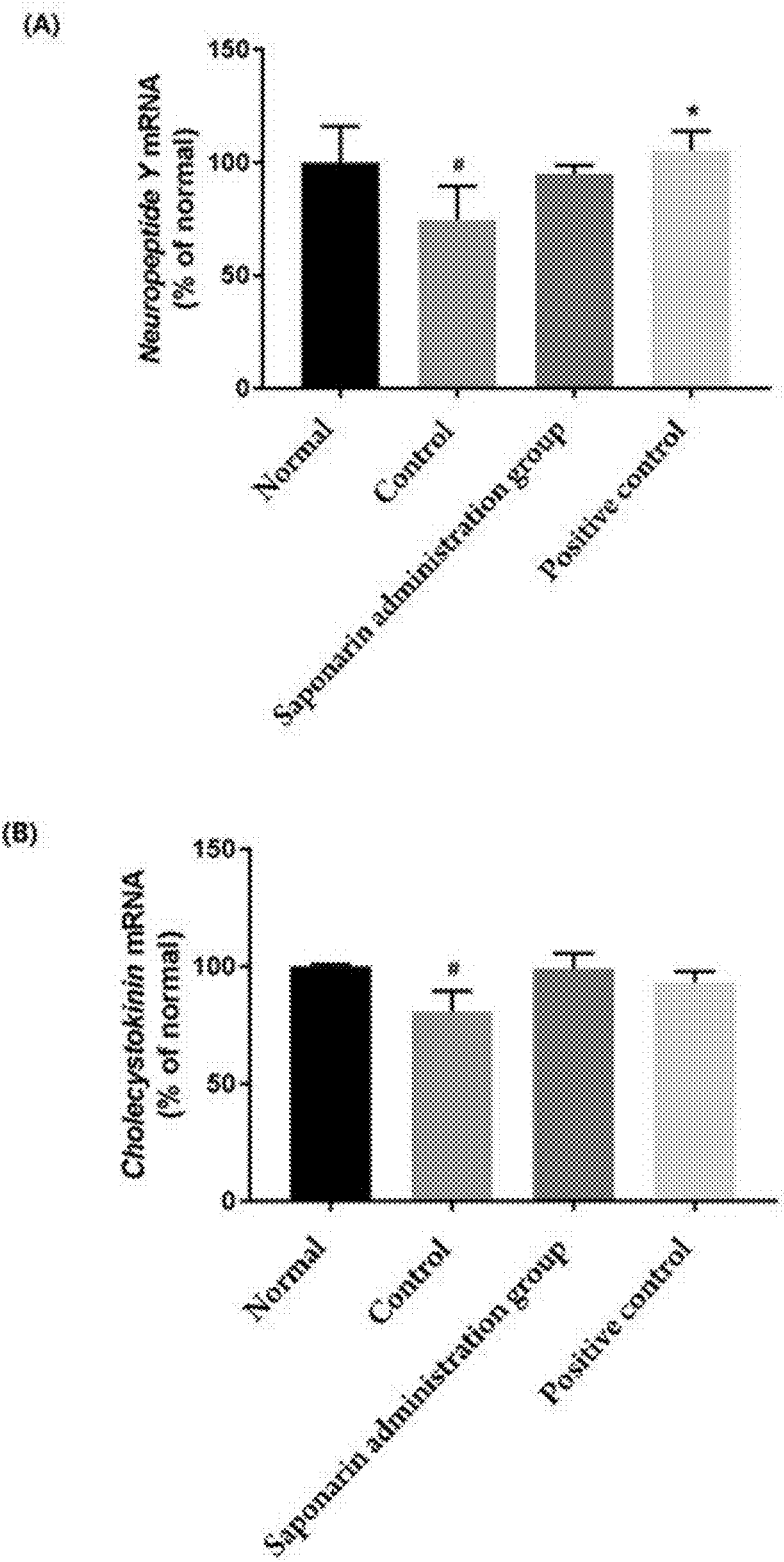
FIG. 5 shows the result of measuring mRNA expression level of (A) neuropeptide Y and (B) cholecystokinin in cerebral cortex of a C57BL/6 mouse induced to have sleep disturbance by caffeine, in which the cerebral cortex was obtained on Day 15 after administering for 14 days 30 mg/kg saponarin or 200 mg/kg St. John's wort (positive control). # indicates that, compared to the normal, the mRNA expression level of (A) neuropeptide Y and (B) cholecystokinin has decreased in statistically significant sense in the control with induced sleep disturbance, in which p<0.05. * indicates that, compared to the control, the mRNA expression level of (A) neuropeptide Y or (B) cholecystokinin has increased in statistically significant sense in the saponarin administration group of the present invention and also in the positive control, in which p<0.05.

The result indicates that, as shown in FIG. 5, the mRNA expression of neuropeptide Y and cholecystokinin has decreased in statistically significant sense in the control. On the other hand, it was found that the saponarin group and the group administered with positive control show increased expression or tend to show increased expression in statistically significant sense.

Example 5. Determination of Effect Flavonoid Compound on mRNA Expression of GABA A α1 Receptor in C57BL/6 Mouse with Induced Sleep Disturbance To examine any influence of saponarin exhibited on the mRNA expression of GABA A α1 receptor in cerebral cortex of C57BL/6 mouse which has been induced to have sleep disturbance, the animal was orally administered, according to the aforementioned experimental method, with a test sample and then intraperitoneally administered with caffeine for 14 days. Thereafter, cerebral cortex was collected by autopsy of the mouse to obtain RNA. cDNA was then prepared and mRNA expression of GABA A α1 receptor was analyzed by using real-time gene analyzer.

Figure 6:
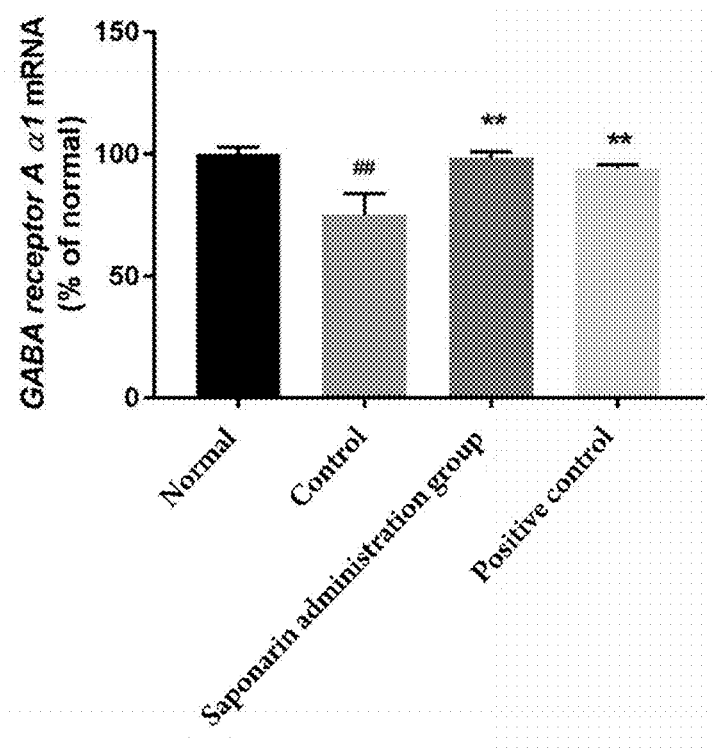
FIG. 6 shows the result of measuring mRNA expression level of GABA A α1 receptor in cerebral cortex of a C57BL/6 mouse induced to have sleep disturbance by caffeine, in which the cerebral cortex was obtained on Day 15 after administering for 14 days 30 mg/kg saponarin or 200 mg/kg St. John's wort (positive control). ## indicates that, compared to the normal, the mRNA expression level of GABA A α1 receptor has decreased in statistically significant sense in the control with induced sleep disturbance, in which p<0.01. ** indicates that, compared to the control, the mRNA expression level of GABA A α1 receptor has increased in statistically significant sense in the saponarin administration group of the present invention and also in the positive control, in which p<0.01.

The result indicates that, as shown in FIG. 6, the mRNA expression of GABA A a1 receptor has decreased in significant sense in the control. On the other hand, it was found that the saponarin group and the group administered with positive control show increased mRNA expression of GABA A α1 receptor in significant sense.

Example 6. Determination of Effect of Flavonoid Compound on Wake Time During Sleep of SD Rat with Induced Sleep Disturbance To determine the effect of saponarin exhibited on wake time during sleep of a SD rat with induced sleep disturbance, via oral administration according to the aforementioned experimental method, SD rats of the normal and the stress control were orally administered with a solvent while the saponarin administration group was orally administered with 30 mg/kg saponarin and the positive control was administered with 200 mg/kg St. John's wort. After 30 minutes, foot pad electric shock was applied to the SD rats to induce for 5 days sleep disturbance caused by stress. Wake time was then measured for each rat.

Figure 8:
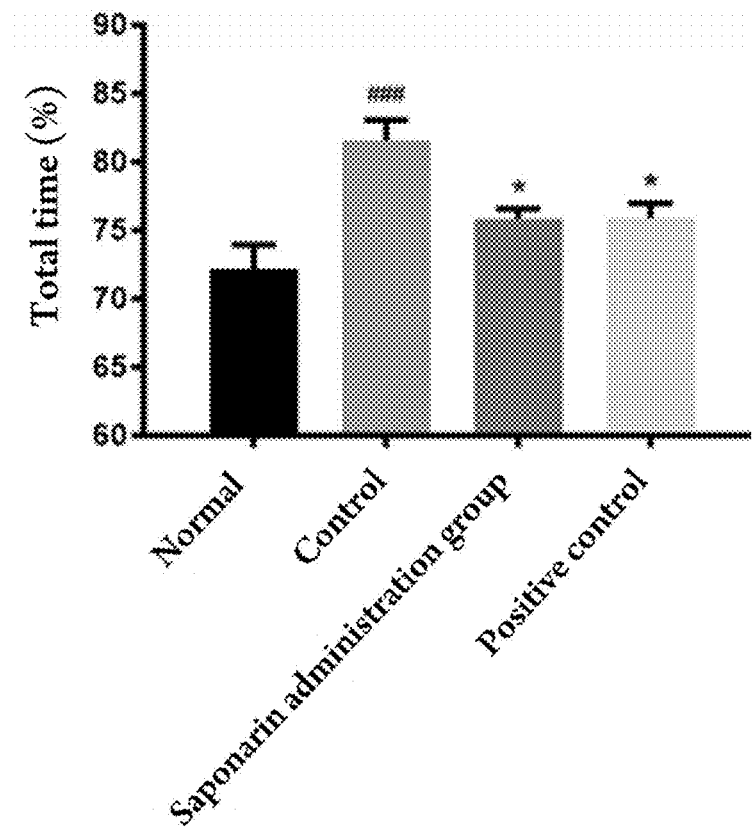
FIG. 8 shows the result of determining wake time by EEG, which was measured after administering for 5 days 30 mg/kg saponarin or 200 mg/kg St. John's wort (positive control) to a SD rat induced to have sleep disturbance by stress. ### indicates that, compared to the normal, the control with sleep disturbance induced by stress has longer wake time in statistically significant sense, in which p<0.001. * indicates that, compared to the control induced to have sleep disturbance by stress, the saponarin administration group and the positive control (St. John's wort administration group) have shorter wake time in statistically significant sense, in which p<0.05.

As the result is shown in FIG. 8, it was found that the wake time during sleep has decreased in significant sense in the saponarin group and the group administered with positive control compared to the stress control.

Example 7. Determination of Effect of Flavonoid Compound on REM Sleep Time During Sleep of SD Rat with Induced Sleep Disturbance To determine the effect of saponarin exhibited on REM sleep time of a SD rat with induced sleep disturbance, according to the aforementioned experimental method, the test sample and stress were applied for 5 days, and then REM sleep time of rat was measured.

Figure 9:
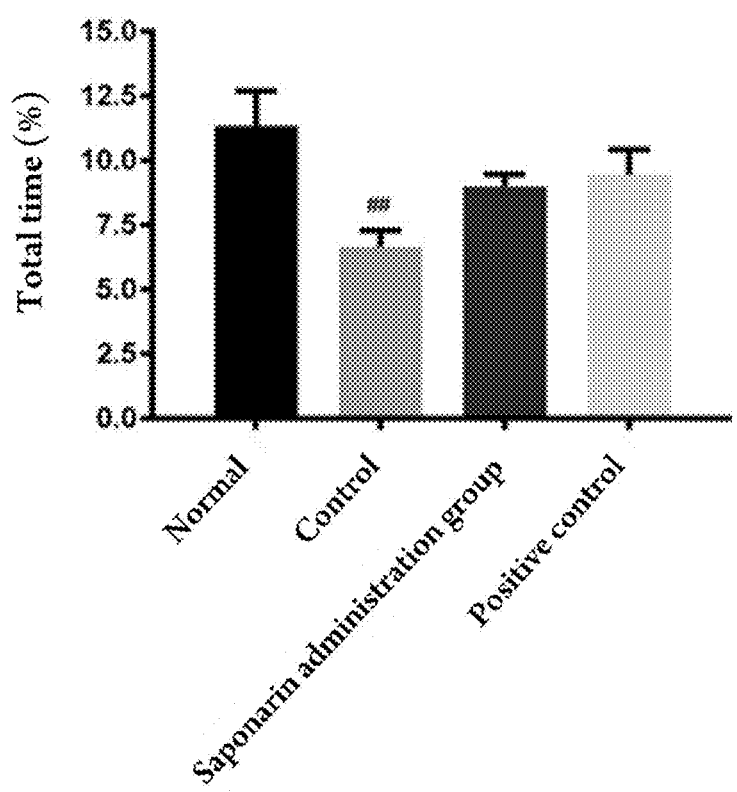
FIG. 9 shows the result of determining REM time by EEG, which was measured after administering for 5 days 30 mg/kg saponarin or 200 mg/kg St. John's wort (positive control) to a SD rat induced to have sleep disturbance by stress. ## indicates that, compared to the normal, the control with sleep disturbance induced by stress has shorter REM time in statistically significant sense, in which p<0.01.

As the result is shown in FIG. 9, it was found that the REM sleep time tends to increase in the group administered with saponarin compared to the stress control.

Example 8. Determination of Effect of Flavonoid Compound on NonREM Sleep Time During Sleep of SD Rat with Induced Sleep Disturbance To determine the effect of saponarin exhibited on Non-REM sleep time of a SD rat with induced sleep disturbance, according to the aforementioned experimental method, the test sample and stress were applied for 5 days, and then NonREM sleep time of rat was measured.

Figure 10:
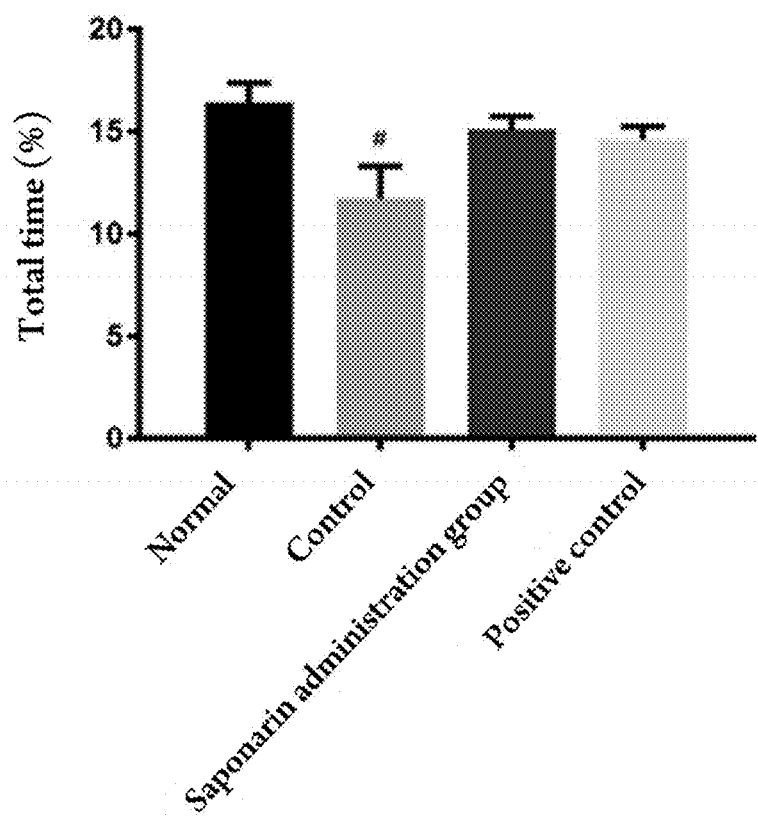
FIG. 10 shows the result of determining NonREM time by EEG, which was measured after administering for 5 days 30 mg/kg saponarin or 200 mg/kg St. John's wort (positive control) to a SD rat induced to have sleep disturbance by stress. # indicates that, compared to the normal, the control with sleep disturbance induced by stress has shorter NonREM time in statistically significant sense, in which p<0.05.

As the result is shown in FIG. 10, it was found that the NonREM sleep time tends to increase in the group administered with saponarin compared to the stress control.

A sequence listing electronically submitted with the present application on Apr. 12, 2021 as an ASCII text file named 20210412_Q50921GR05_TU_SEQ, created on Apr. 8, 2021 and having a size of 2,000 bytes, is incorporated herein by reference in its entirety.

---

What is claimed is:

1. A method for treating sleep disturbance, the method comprising administering to a subject in need thereof a composition comprising an effective amount of saponarin of Chemical Formula 1, a salt thereof acceptable for use in food, or a hydrate thereof as an effective component:

[Chemical formula 1]

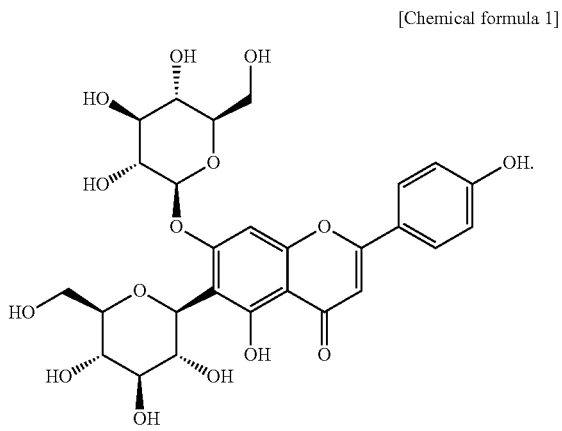 [SMILES: O=c1cc(-c2ccc(O)cc2)oc2cc(O[C@@H]3O[C@H](CO)[C@@H](O)[C@H](O)[C@H]3O)c([C@@H]3O[C@H](CO)[C@@H](O)[C@H](O)[C@H]3O)c(O)c12]

wherein the sleep disturbance is insomnia caused by stress and/or caffeine.

2. The method of claim 1, wherein the sleep disturbance is the insomnia caused by the stress.

3. The method of claim 1, wherein the sleep disturbance is the insomnia caused by the caffeine.

4. The method of claim 1, wherein the composition is a functional health food composition comprising at least one selected from a nutritional supplement, a vitamin, an electrolyte, a flavor, a coloring agent, an enhancing agent, pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink in addition to the effective component.

5. The method of claim 4, wherein the functional health food composition is produced in any one formulation selected from a powder, a granule, a pill, a tablet, a capsule, a candy, a syrup, and a drink.

6. The method of claim 1, wherein the composition is a pharmaceutical composition comprising a pharmaceutically acceptable carrier, vehicle, or diluent in addition to the effective component.

* * * * *